US010925493B2

(12) United States Patent
Forsyth et al.

(10) Patent No.: US 10,925,493 B2
(45) Date of Patent: Feb. 23, 2021

(54) FIDUCIAL MARKERS FOR FLUORESCENT 3D IMAGING

(71) Applicant: Lantos Technologies Inc., Cambridge, MA (US)

(72) Inventors: Alison M. Forsyth, Boston, MA (US); Daniel Vlasic, Cambridge, MA (US); Ben Frantzdale, Shrewsbury, MA (US); Alban de Brouchoven de Bergeyck, Cambridge, MA (US); Xiaowei Chen, Cambridge, MA (US); Manas Menon, Boston, MA (US); Federico Frigerio, Chestnut Hill, MA (US)

(73) Assignee: LANTOS TECHNOLOGIES, INC., Derry, NH (US)

(*) Notice: Subject to any disclaimer, the term of this patent is extended or adjusted under 35 U.S.C. 154(b) by 423 days.

(21) Appl. No.: 14/214,414

(22) Filed: Mar. 14, 2014

(65) Prior Publication Data
US 2014/0276005 A1    Sep. 18, 2014

Related U.S. Application Data

(60) Provisional application No. 61/790,491, filed on Mar. 15, 2013.

(51) Int. Cl.
*A61B 5/00* (2006.01)
*A61B 5/107* (2006.01)
(Continued)

(52) U.S. Cl.
CPC ............ *A61B 5/0071* (2013.01); *A61B 1/227* (2013.01); *A61B 5/0064* (2013.01);
(Continued)

(58) Field of Classification Search
None
See application file for complete search history.

(56) References Cited

U.S. PATENT DOCUMENTS

| 3,790,653 A | 2/1974 | Barkey et al. |
| 4,643,733 A | 2/1987 | Becker |

(Continued)

FOREIGN PATENT DOCUMENTS

| CA | 2840602 A1 | 1/2013 |
| CN | 102177733 A | 9/2011 |

(Continued)

OTHER PUBLICATIONS

WelchAllyn CompacVideo Otoscope Model 23120 (NTSC) and 23120P (PAP), Operating Instruction Manual, 2000, 16 pages.
(Continued)

*Primary Examiner* — Serkan Akar
(74) *Attorney, Agent, or Firm* — GTC Law Group PC & Affiliates

(57) ABSTRACT

In one aspect, there is provided an apparatus. The apparatus may include a balloon membrane. The balloon membrane may include an opening, an exterior surface, and an interior surface. The interior surface may include one or more fiducial markers forming a pattern detectable by a scanner imaging the interior surface of the balloon membrane. Scanned portions of the interior surface of the balloon membrane may be combined based on the fiducial markers forming the pattern. Related methods and articles of manufacture, including computer program products, are also disclosed.

14 Claims, 17 Drawing Sheets

(51) Int. Cl.
*A61B 1/227* (2006.01)
*C08K 3/04* (2006.01)

(52) U.S. Cl.
CPC .......... *A61B 5/0084* (2013.01); *A61B 5/6817* (2013.01); *A61B 5/1076* (2013.01); *A61B 5/4887* (2013.01); *C08K 3/04* (2013.01); *Y10T 428/1345* (2015.01)

(56) References Cited

U.S. PATENT DOCUMENTS

| | | | |
|---|---|---|---|
| 5,100,587 | A | 3/1992 | Clough et al. |
| 5,504,316 | A | 4/1996 | Bridgelall et al. |
| 5,829,350 | A | 11/1998 | Muchi et al. |
| 6,001,059 | A | 12/1999 | Elliott |
| 8,032,337 | B2 | 10/2011 | Deichmann et al. |
| 8,047,207 | B2 | 11/2011 | Perez et al. |
| 8,107,086 | B2 | 1/2012 | Marini et al. |
| 8,384,916 | B2 | 2/2013 | Hart et al. |
| 8,840,566 | B2 | 9/2014 | Seibel et al. |
| 8,845,526 | B2 | 9/2014 | Hart et al. |
| 9,291,565 | B2 | 3/2016 | Hart et al. |
| 9,592,100 | B2 * | 3/2017 | Olson ............... A61B 90/96 |
| 10,122,989 | B2 | 11/2018 | Fei et al. |
| 10,616,560 | B2 | 4/2020 | Fei et al. |
| 2003/0164952 | A1 | 9/2003 | Deichmann et al. |
| 2004/0107080 | A1 | 6/2004 | Deichmann et al. |
| 2005/0191451 | A1 | 9/2005 | Osika et al. |
| 2007/0106012 | A1 | 5/2007 | Matyjaszewski et al. |
| 2008/0027358 | A1 * | 1/2008 | Gregersen ............ A61B 5/036 600/593 |
| 2008/0058629 | A1 | 3/2008 | Seibel et al. |
| 2009/0171196 | A1 | 7/2009 | Hauck et al. |
| 2009/0245530 | A1 | 10/2009 | Keady |
| 2009/0289938 | A1 | 11/2009 | Paulsen |
| 2009/0296980 | A1 | 12/2009 | Yi |
| 2010/0019170 | A1 | 1/2010 | Hart et al. |
| 2010/0039534 | A1 * | 2/2010 | Hart .................. A61B 1/043 348/234 |
| 2010/0042002 | A1 | 2/2010 | Hart et al. |
| 2010/0168562 | A1 * | 7/2010 | Zhao ................. A61B 34/30 600/426 |
| 2010/0296664 | A1 | 11/2010 | Burgett et al. |
| 2011/0009702 | A1 | 1/2011 | Morishita et al. |
| 2011/0076608 | A1 | 3/2011 | Bergemann et al. |
| 2011/0144480 | A1 | 6/2011 | Lu et al. |
| 2011/0235843 | A1 | 9/2011 | Keady et al. |
| 2011/0290005 | A1 | 12/2011 | Hart et al. |
| 2012/0327426 | A1 | 12/2012 | Hart et al. |
| 2013/0002426 | A1 | 1/2013 | Hart et al. |
| 2013/0002824 | A1 | 1/2013 | Hart et al. |
| 2013/0027516 | A1 | 1/2013 | Hart et al. |
| 2013/0078555 | A1 * | 3/2013 | Orihara ............... G03F 1/24 430/5 |
| 2013/0261655 | A1 * | 10/2013 | Drasler ............... A61M 29/02 606/194 |
| 2014/0272221 | A1 | 9/2014 | Forsyth et al. |
| 2014/0275974 | A1 * | 9/2014 | Samuels ............. A61B 5/1076 600/417 |
| 2014/0276105 | A1 | 9/2014 | De Brouchoven et al. |
| 2014/0330133 | A1 * | 11/2014 | Stern .................. A61B 5/1076 600/479 |
| 2015/0017779 | A1 | 1/2015 | Kim |
| 2015/0036146 | A1 * | 2/2015 | Staloff ............... G01B 9/02091 356/479 |
| 2016/0150949 | A1 | 6/2016 | Patterson et al. |
| 2017/0104977 | A1 | 4/2017 | Fei et al. |
| 2018/0178419 | A1 | 6/2018 | Fei et al. |
| 2018/0319047 | A1 | 11/2018 | Fei et al. |
| 2019/0014309 | A1 | 1/2019 | Fei et al. |

FOREIGN PATENT DOCUMENTS

| | | |
|---|---|---|
| CN | 103974183 A | 8/2014 |
| CN | 104333826 A | 2/2015 |
| CN | 104796806 A | 7/2015 |
| CN | 104936054 A | 9/2015 |
| JP | H08243262 A | 9/1996 |
| WO | WO-2012115863 A2 | 8/2012 |
| WO | 2013002935 A1 | 1/2013 |
| WO | WO-2013003416 A2 | 1/2013 |
| WO | 2014145026 A2 | 9/2014 |
| WO | 2014145058 A1 | 9/2014 |
| WO | 2014145077 A1 | 9/2014 |
| WO | 2015017779 A1 | 2/2015 |
| WO | 2016086005 A1 | 6/2016 |
| WO | 2017062868 A1 | 4/2017 |
| WO | 2017062868 A8 | 4/2017 |
| WO | 2018118772 A9 | 6/2018 |

OTHER PUBLICATIONS

U.S. Appl. No. 14/214,396, filed Mar. 14, 2014.
U.S. Appl. No. 14/214,406, filed Mar. 14, 2014.
International Search Report and Written Opinion dated Jul. 31, 2014 for PCT application No. PCT/US2014/029712.
International Search Report and Written Opinion dated Aug. 7, 2014 for PCT application No. PCT/US2014/029738.
International Search Report and Written Opinion dated Sep. 11, 2014 for PCT application No. PCT/US2014/029662.
Park, "3D scan designs headphones just for you", [retrieved Dec. 19, 2016], http://www.unitedsciences.com/151-2, Jan. 10, 2015, 2 pages.
PCT/US15/62464, "International Application Serial No. PCT/US15/62464, International Preliminary Report on Patentability, dated May 30, 2017", Lantos Technologies Inc., 5 pages.
PCT/US15/62464, "International Application Serial No. PCT/US15/62464, International Search Report and Written Opinion dated Mar. 31, 2016", Lantos Technologies Inc., 7 pages.
PCT/US16/56132, "International Application Serial No. PCT/US16/56132, International Preliminary Report on Patentability and Written Opinion dated Apr. 19, 2018", Lantos Technologies Inc., 7 Pages.
PCT/US16/56132, "International Application Serial No. PCT/US16/56132, International Search Report and Written Opinion dated Jan. 26, 2017", Lantos Technologies, Inc., 8 pages.
PCT/US17/67010, "International Application Serial No. PCT/US17/67010, International Search Report and the Written Opinion dated Mar. 9, 2018.", Lantos Technologies Inc., 11 pages.
PCT/US2014/029662, "International Application Serial No. PCT/US2014/029662, International Preliminary Report on Patentability dated Sep. 24, 2015", 5 pages.
PCT/US2014/029712, "International Application Serial No. PCT/US2014/029712, International Preliminary Report on Patentability dated Sep. 24, 2015", 5 pages.
PCT/US2014/029738, "International Application Serial No. PCT/US2014/029738 International Preliminary Report on Patentability dated Sep. 24, 2015", 5 pages.
16854493.0, "European Application Serial No. 16854493.0, Extended European Search Report dated May 17, 2019", Lantos Technologies, Inc., 10 pages.
PCT/US17/67010, "International Application Serial No. PCT/US17/67010, International Preliminary Report on Patentability dated Jul. 4, 2019", Lantos Technologies, Inc., 8 pages.
17885270.3, "European Application Serial No. 17885270.3, Extended European Search Report dated May 19, 2020", Lantos Technologies, Inc., 8 pages.

* cited by examiner

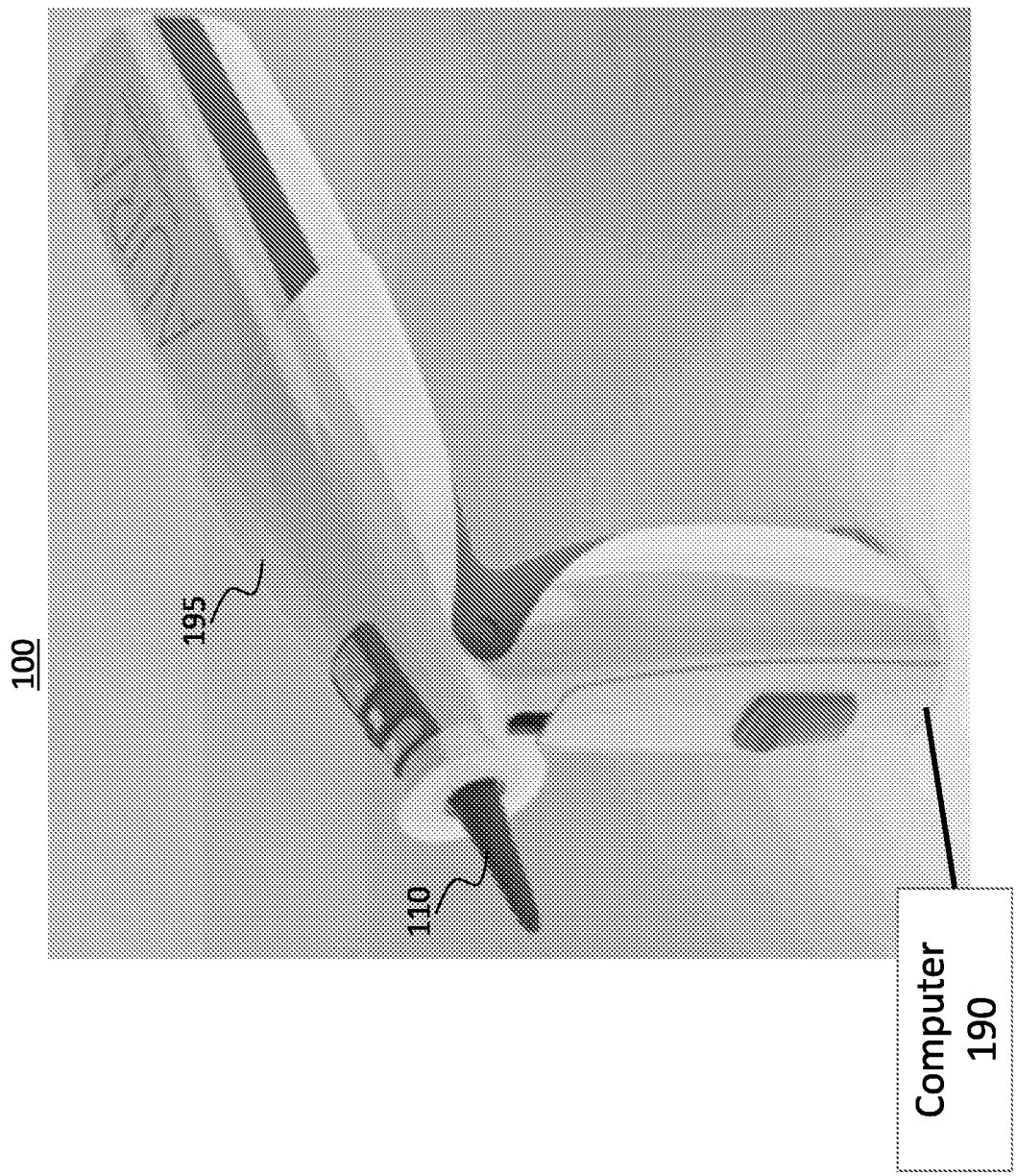

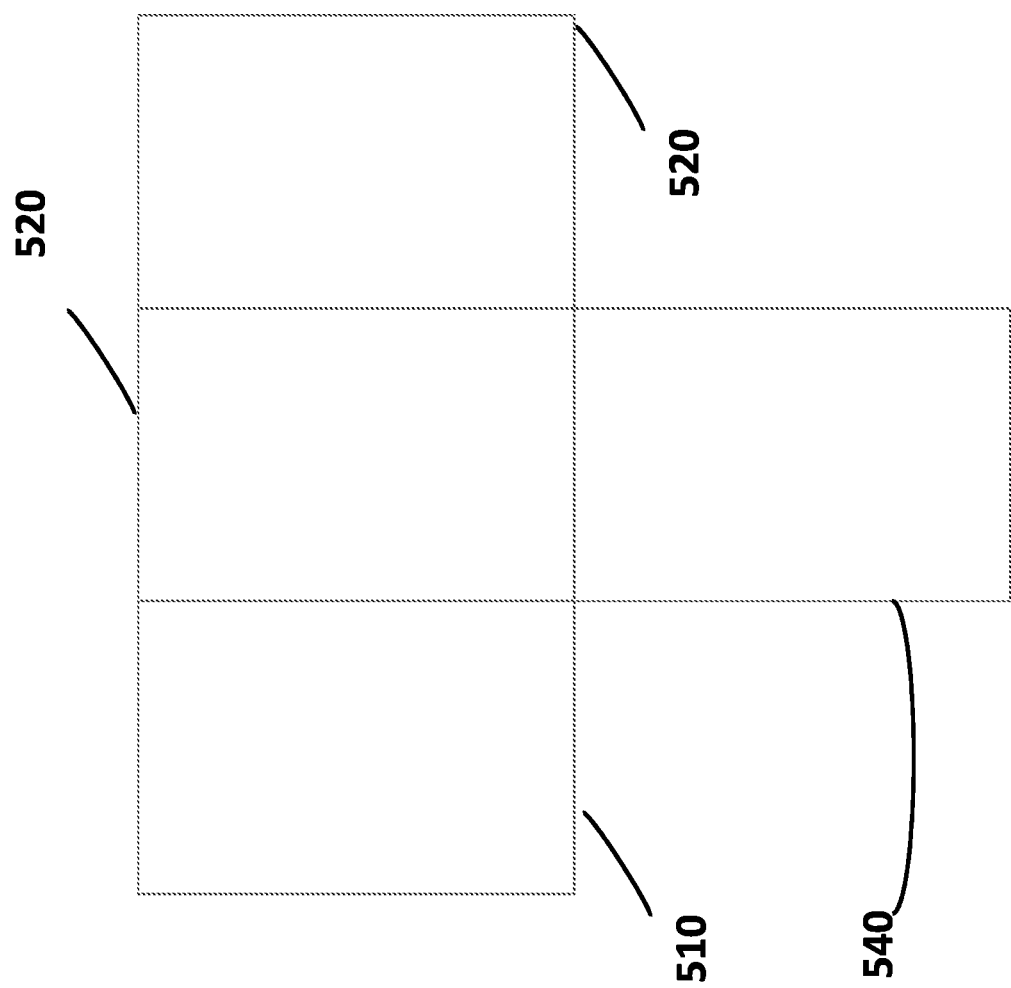

FIDUCIAL MARKERS FOR FLUORESCENT 3D IMAGING

CROSS-REFERENCE TO RELATED APPLICATION

This application claims priority to U.S. Provisional Patent Application Ser. No. 61/790,491, titled "Apparatus and Methods for Probing and Measuring Anatomical Cavities," filed Mar. 15, 2013, the disclosure of which is hereby incorporated by reference herein.

FIELD

The subject matter described herein relates to probing and measuring cavities and, in particular, fiducial markers used in imaging of cavities, such as a human ear canal.

BACKGROUND

Devices can be created to fit into anatomical cavities, such as the human ear canal. When creating such devices, having a comfortable and snug fit between a device and the cavity into which it is placed can enhance the performance of the device.

Traditional methods of probing and measuring sensitive cavities, such as anatomical cavities, include creating impressions of the cavity. Creating or taking an impression includes injecting a material into the cavity. The material is allowed to harden and conform to the shape of the cavity, and then the material is extracted from the cavity. An impression created this way can cause complications or pain when a blocking device is inserted into the ear to prevent the impression material from contacting the tympanic membrane, when the impression material is injected into the cavity, when the material is hardening, and/or when the impression is extracted. Such actions can exert pressure on the walls of the cavity in a painful or damaging way or result in inaccuracies. The impression taking process may also be somewhat limited when it comes to consistency. Each Audiologist may apply a different amount of pressure and use different techniques. This may result in less consistent impressions and corresponding devices.

SUMMARY

Methods, systems, and apparatus, including computer program products, are provided for scanning techniques for probing and measuring anatomical cavities.

In some example embodiments, there may be provided an apparatus. The apparatus may include a balloon membrane including an opening, an exterior surface, and an interior surface, the interior surface including one or more fiducial markers forming a pattern detectable by a scanner imaging the interior surface of the inflatable membrane.

In some implementations, the above-noted aspects may further include additional features described herein including one or more of the following. A scanner may be coupled to the opening of the balloon membrane. The scanner may image a plurality of portions of the interior surface including the one or more fiducial markers forming the pattern, when the balloon membrane is inflated with a wavelength-selective medium. The one or more fiducial markers may encode location information indicating relative locations within the pattern. The location information may be encoded based on at least one missing fiducial marker. At least one missing fiducial marker may indicate a relative location on the pattern and on the interior surface of the balloon membrane. The one or more fiducial markers may be applied to the interior surface of the inflatable membrane by at least one of pad-printing or photo-bleaching.

In some example embodiments, a method may be provided. The method may include receiving a first data representative of a first scanned portion of an interior surface of a balloon membrane and a second data representative of a second scanned portion of the interior surface of the balloon membrane, the interior surface including a pattern comprising one or more fiducial markers; detecting from the first data a first portion of the pattern, the first portion indicating a location of the first portion within the pattern and the interior surface of the balloon membrane; detecting from the second data a second portion of the pattern, the second portion indicating another location of the second portion within the pattern and the interior surface of the balloon membrane; and combining, based on the first portion of the pattern and the second portion of the pattern, the first data and the second data to form a three dimensional representation of the interior surface.

In some implementations, the above-noted aspects may further include additional features described herein including one or more of the following. A scanner may scan the first scanned portion of the interior surface of the balloon membrane and the second scanned portion of the interior surface of the balloon membrane. The scanner may be coupled to an opening of the balloon membrane. The scanner may image a plurality of portions of the interior surface including the first scanned portion and the second scanned portion, when the balloon membrane is inflated with a wavelength-selective medium. The one or more fiducial markers may encode location information indicating relative locations within the pattern. The location information may be encoded based on at least one missing fiducial marker. The at least one missing fiducial marker may indicate a relative location on the pattern and on the interior surface of the balloon membrane. The one or more fiducial markers may be applied to the interior surface of the inflatable membrane by at least one of pad-printing or photo-bleaching.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

DESCRIPTION OF DRAWINGS

In the drawings,

FIG. 1A depicts an example of a system including a three-dimensional (3D) scanner having an inflatable membrane;

FIG. 5F depicts an example of scanner data combined based on location information contained in a fiducial marker pattern.

Figure 1B:
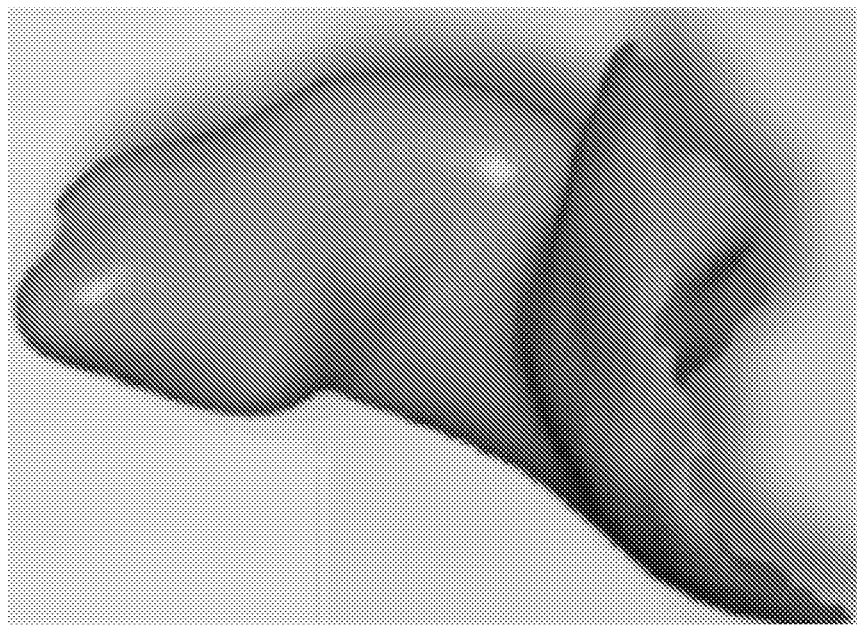
FIG. 1B depicts an example 3D rendering of a cavity formed based on scanner data collected by the 3D scanner of FIG. 1A.

Like labels are used to refer to same or similar items in the drawings.

DETAILED DESCRIPTION

Injection of materials into sensitive cavities, such as anatomical cavities, can, as noted, can cause pain and/or damage to the cavity. Alternative methods for probing and measuring cavities may include scanning techniques utilizing light. Described herein are methods, apparatus, and systems for fiducial markers used to combine scan data obtained from scans of an anatomical cavity, such as the human ear canal.

FIG. 1A depicts a system 100 including an inflatable membrane 110, in accordance with some example implementations. The system 100 may generate three-dimensional (3D) scans of a cavity, such as an ear cavity.

System 100 may include a 3D scanner 195 including inflatable membrane 110 and a processor 190, such as computer. The processor 190 may process scanner data generated by 3D scanner 195 during a scan of the cavity. The processor 190 may form an output, such as a 3D impression of the scanned cavity. FIG. 1B depicts an example of a 3D surface formed by processor 190 based on scan data provided by 3D scanner 195. The 3D surface may model the cavity being scanned, such as an ear cavity, and this 3D surface may be provided to a manufacturer, 3D printer, and the like to form an object. In the case of the ear, the object may be an earpiece.

The subject matter disclosed herein may provide fiducial markers on the interior surface of the inflatable membrane 110. When 3D scanner 195 scans different portions of the interior surface of the membrane 110, fiducial markers allow the scanned portions to be stitched together or combined to form a 3D surface.

In some example embodiments, fiducial markers may be applied on at least the interior surface of an inflatable membrane 110. In some example embodiments, a known pattern may be used for the fiducial markers. Moreover, the pattern may encode location information to allow assembling scanned portions based on the fiducial markers.

Before providing additional description regarding the disclosed fiducial markers, the following provides additional examples regarding an example implementation of 3D scanner 195.

Figure 1C:
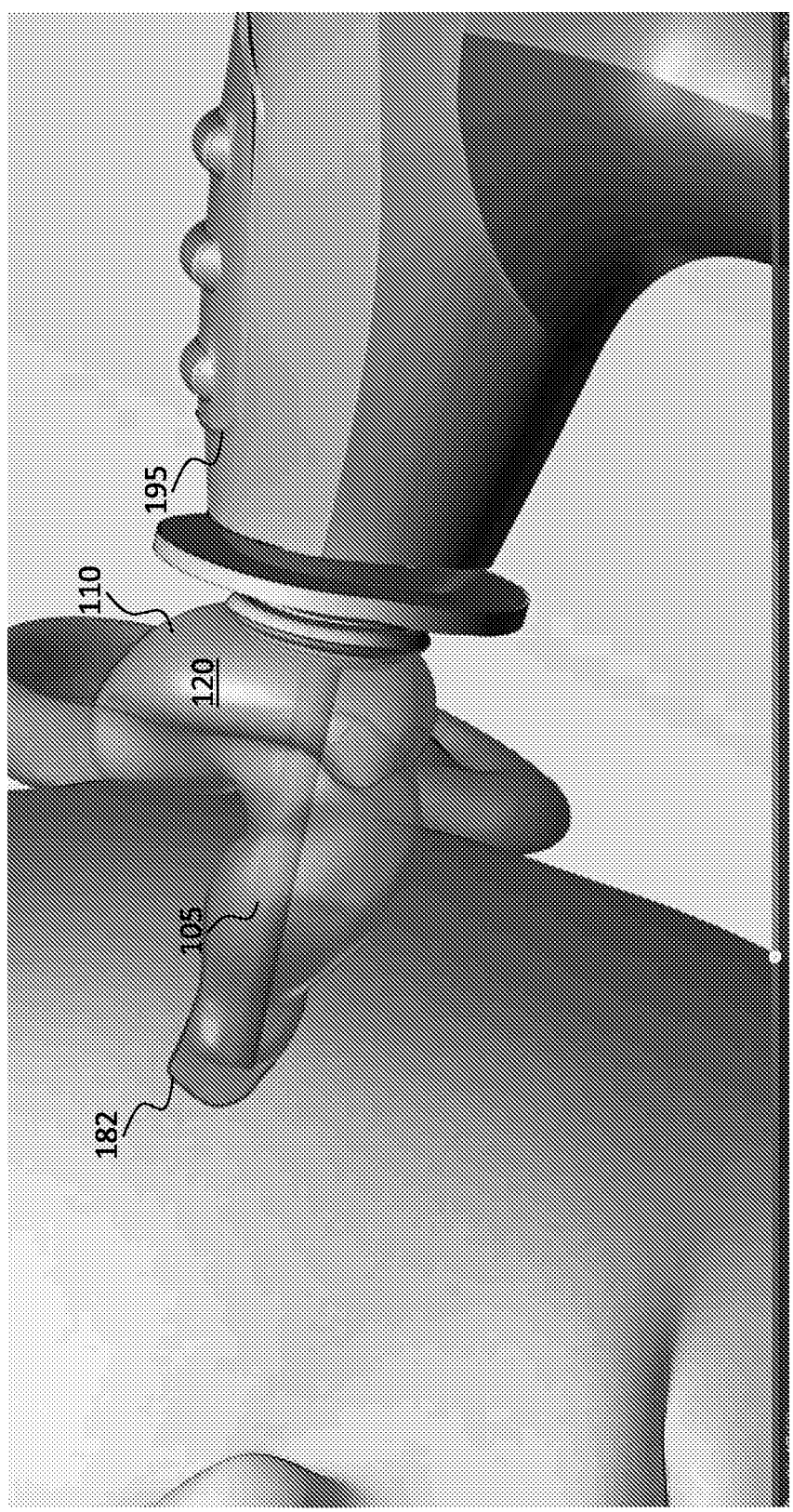
FIGS. 1C-D depict examples of a system including a 3D scanner having an inflatable membrane.

FIG. 1C depicts a portion of 3D scanner 195 after being inserted into an ear cavity 182 and after a medium 120 is transferred into the interior of the inflatable membrane 110, so that the inflatable membrane 110 conforms to the ear cavity 182 (or portion of the ear cavity and/or any other cavity or surface being scanned). For example, the medium 120 may be pumped into or placed in the membrane 110, so that membrane 110 conforms to the cavity being scanned. At this point, scanner element 105 may scan the interior surface of the inflatable membrane 110 which when inflated with the medium 120 conforms to the ear cavity 182. The scanner element 105 may move within the membrane 110 to scan the interior surface of membrane 110. In this way, scanner element 105 may scan the interior surface of the membrane 110 and thus ear cavity 182.

The scanner element 105 may generate a 2D image of the inflatable membrane approximating a snap shot of the anatomical cavity. Each pixel of the 2D image may then be associated with distance information obtained during a scan, that is the distance from the scanner element 105 to the scanned portion of the membrane. The combination of the 2D image and distance information for each pixel of the 2D image may correspond to 3D data (for example, a 3D surface representative of the scanned cavity). In some implementations, the distance information determined from scanning data can correlate to groups of pixels, instead of a single pixel, on the 2D image.

Medium 120 may be a liquid, a gas, a gel, a hydrogel, and/or any combination of the four. The medium 120 may include additives dissolved into, or suspended in, the medium 120 to provide properties, such as selective absorption where one or more wavelengths of light are absorbed more than one or more other wavelengths. To illustrate, medium 120 may include a colored dye, suspension, a luminescent substance, and/or a fluorescent substance (and/or any other material having selective wavelength properties). Moreover, the selective wavelength properties may, as described further below, allow 3D scanner and/or processor 190 to determine the shape of, distance to, and/or other properties of the scanned interior surface of membrane 110.

The inflatable membrane 110 may be implemented as any viscoelastic, elastic, plastic, and/or any other material that may be inflated to conform to the cavity, when the membrane 110 is inserted and inflated with medium 120. When the cavity corresponds to an ear canal, membrane 110 may have an inflated 3D shape and size that is substantially adapted to the ear cavity, although the membrane 110 may be used with other cavities and forms as well including a stomach, an esophagus, a bladder, and so forth. The membrane 110 may also include, or be coated with, a material to make the membrane fluoresce in the presence of white light, light of a particular wavelength, or a range of wavelengths, as further described below. In some example embodiments, membrane 110 may, as noted, also have fiducial marks imprinted on the interior of the membrane. In some implementations, the inflatable membrane may have a balloon-like shape with an opening, an interior surface, and an exterior surface. In some implementations, scanning the interior membrane 110, rather than the ear cavity directly, may reduce (if not eliminate) the interference caused by artifacts, such as ear hair, wax, and the like, and may thus improve the quality of the cavity scan.

Figure 1D:
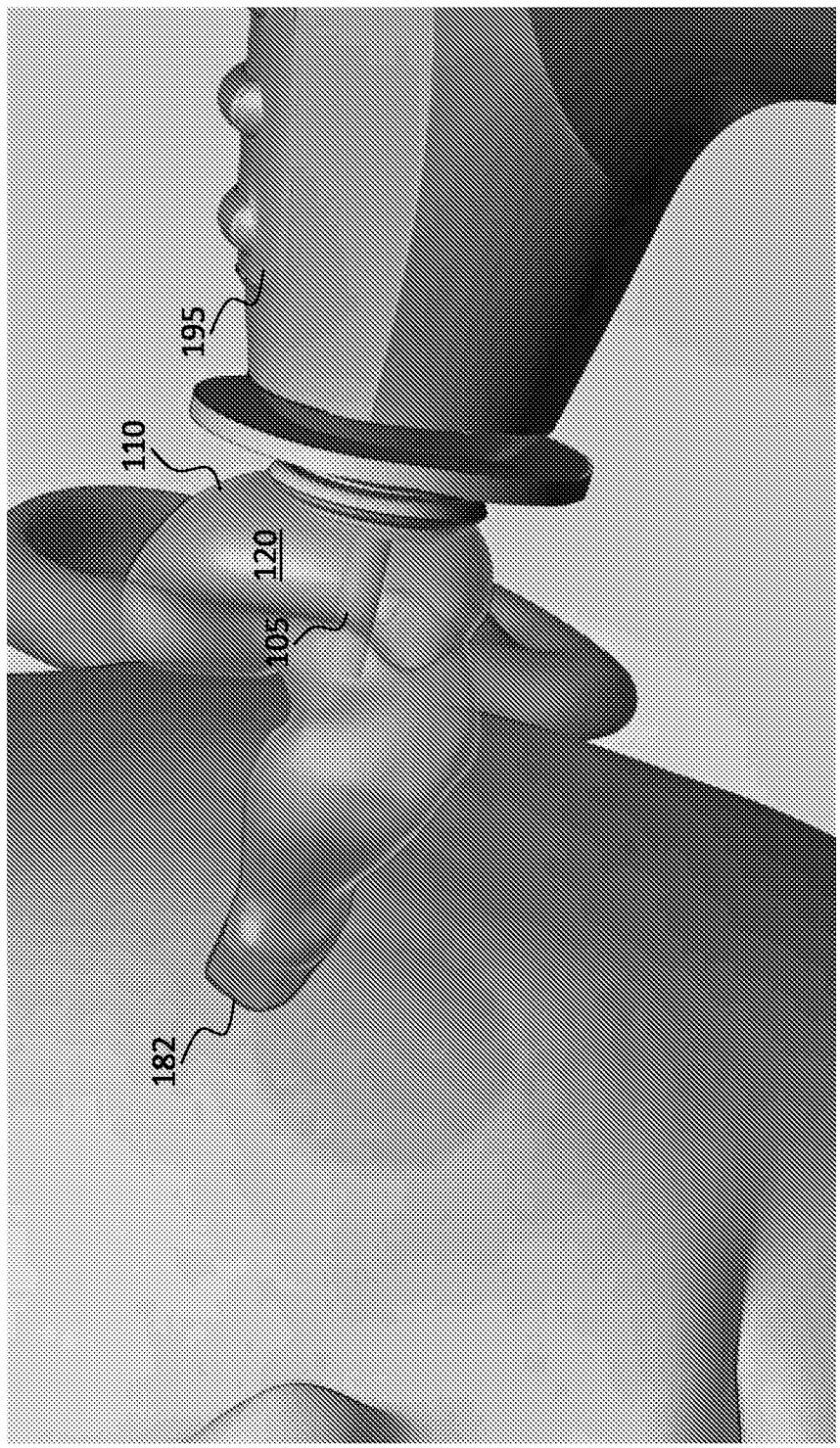

FIG. 1D depicts scanner element 105 after the scanner element has moved towards the opening of the cavity as part of the cavity scanning process. While scanning, scanner element 105 may scan one or more portions of the interior surface of the membrane 110, and element 105 may move within the membrane (and ear cavity 182) to image some (if not all) of the inner membrane 110/cavity 182. The scanner data collected by 3D scanner 195 may then be provided to one or more processors, such as computer 190 and/or a cradle-like device including other/intermediary processor(s), to form a 3D surface or impression representative of the cavity as depicted at FIG. 1B, although some (if not all) of the processing may be performed by a processor contained in the 3D scanner 195 as well.

Figure 1E:
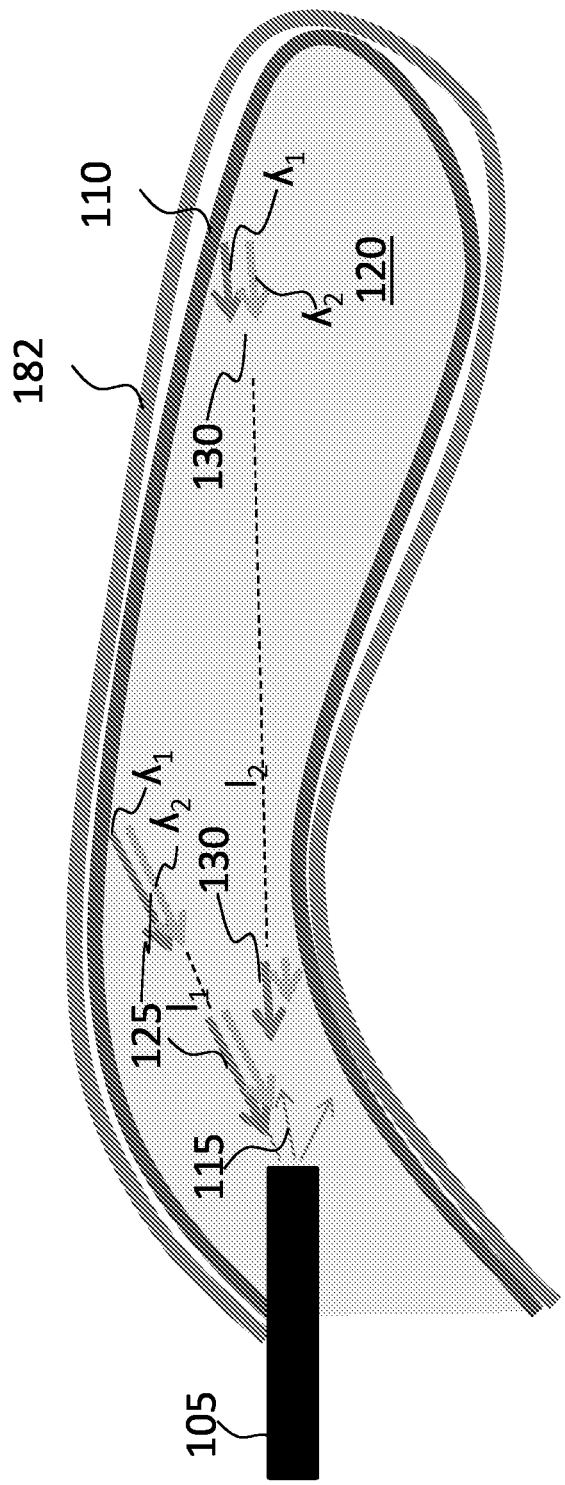
FIG. 1E shows a block diagram of a tip portion of the 3D scanner of FIGS. 1A, C, and D.

FIG. 1E shows a block diagram of the tip portion of 3D scanner 195 and, in particular, scanner element 105, inflatable membrane 110, and medium 120. The 3D scanner 195 and/or the scanner element 105 may include at least one light source, such as a light emitting diode, for emitting light 115 into the inflatable membrane 110, including medium 120. The scanner element 105 may also collect and/or detect light 125 and 130 that is emitted from fluorescent material in, or on, the inflatable membrane 110. The light 115 emanating from scanner element 105 may comprise light used to excite the fluorescent material in, or on, the inflatable membrane 110. Further, light from the fluorescent material in, or on, the inflatable membrane 110 may be referred to as "fluoresced" light, i.e., light resulting from the interaction of the fluorescent material with the light from scanner element 105.

The inflatable membrane 110 may include a fluorescent material, such as one or more fluorescent dyes, pigments, or other coloring agents. The fluorescent material can be homogenously dispersed within the inflatable membrane 110, although the fluorescent material may be applied in other ways as well (for example, the fluorescent material may be pad printed onto the surface of the inflatable membrane). The fluorescent material may be selected so that the fluorescent material is excited by one or more wavelengths of light 115 emitted by the scanner element 105. Once the fluorescent material is excited by light 115, the fluorescent material may emit light at two or more wavelengths $\lambda_1$, $\lambda_2$, or a range of wavelengths. For example, wavelength $\lambda_1$ may represent a range of wavelengths associated generally with red, although wavelength $\lambda_1$ may be associated with other parts of the spectrum as well.

As the two or more wavelengths 125 transmit back through the absorbing medium 120, absorbing medium 120 may absorb one or more of the wavelengths of light $\lambda_1$, $\lambda_2$ to a greater degree than one or more other wavelengths of the light. The absorbing medium 120 used in the system 100 may also be selected to optimally and preferentially absorb one or more of the wavelengths or a range of wavelengths of light from the fluorescent material of the inflatable membrane. By selecting an absorbing medium that complements the fluorescent material, the scan data collected by the 3D scanner may be more accurate.

When the tip portion 100 of 3D scanner 195 is inserted into ear cavity 182, 3D scanner 195 may be inserted into medium 120 into inflatable membrane 110 until the inflatable membrane 110 conforms to the surface of the cavity 182. Once the inflatable membrane 110 is fully inflated, 3D scanner and/or scanner element 105 may include a light emitting diode that generates light 115. Light 115 may travel from the scanner element 105, through medium 120, and excite the fluorescent material on, or in, a portion of the inflatable membrane 110. The light emitted from the fluorescent material on, or in, the inflatable membrane 110 may include at least two wavelengths of light. One of the wavelengths of light or some ranges of wavelengths of light emitted by the fluorescent material may be selectively absorbed by the absorbing medium 120. The light $\lambda_1$, $\lambda_2$ or ranges of light, may then be received by the scanner element 105, and the ratio of the intensities of light $\lambda_1$, $\lambda_2$ or the ratio of the integral area of light found under specific ranges may be measured and recorded by 3D scanner 195 and/or processor 190 to determine a distance from the scanner element 105 to corresponding surface of the membrane 110. The scanner element 105 may move throughout interior of membrane 110 to scan various portions of the surface of the membrane 110 and receive the fluoresced wavelength of light 125, 130 in order to collect data that can be used by the 3D scanner 195 and/or processor 190 to form 3D surface representative of the cavity. Alternatively, or additionally, the scanner element 105 may include optical, electronic, or mechanical means of focusing and directing the light used to excite the fluorescent material. Although the scanner element 105 may include one or more components, such as one or more light emitting diodes, optics, lenses, detectors/CCDs/CMOS sensors, and the like, one or more of these components may be located in other portions of the 3D scanner (for example, a fiber may carry light 115 to scanner element 105).

Figure 1F:
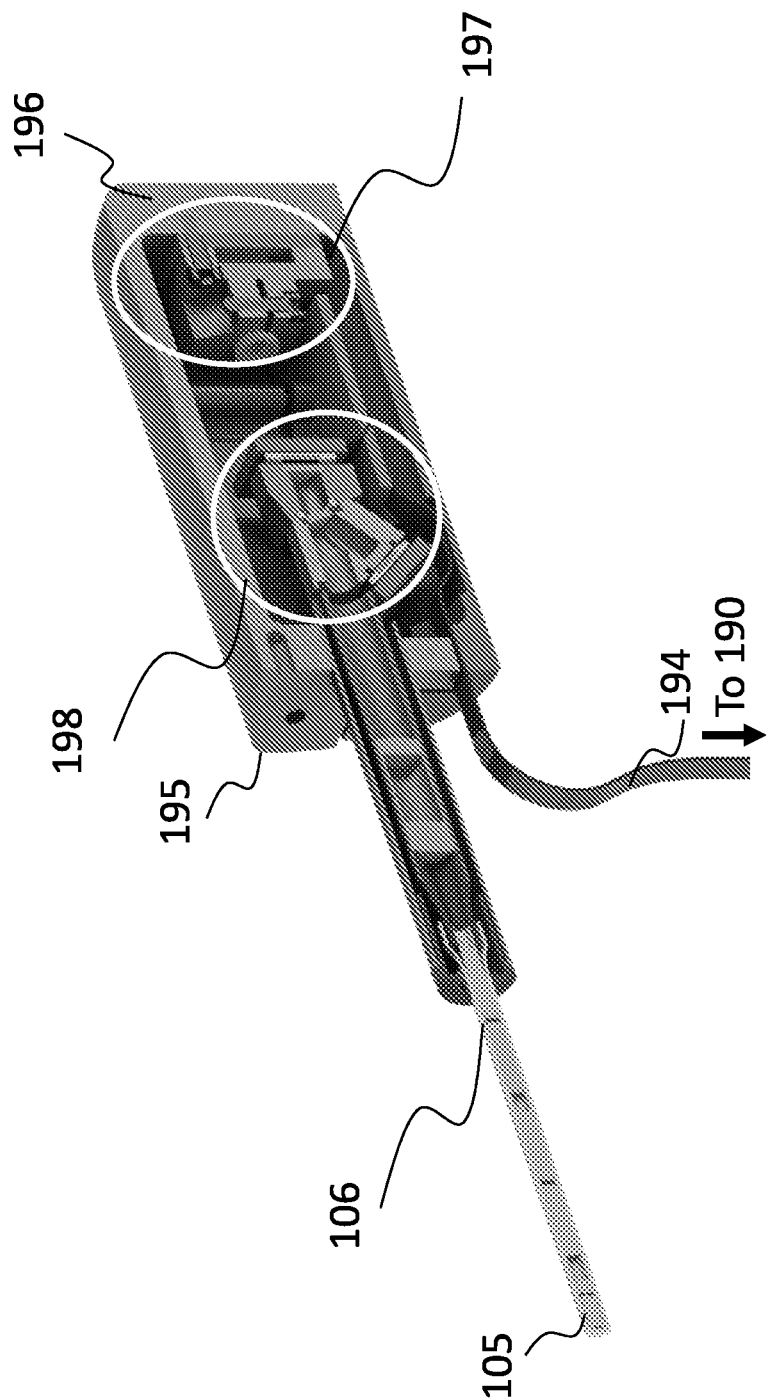
FIG. 1F depicts an example implementation of portions of the 3D scanner.

FIG. 1F depicts an example implementation of the 3D scanner 195 front-end, in accordance with some example implementations. The 3D scanner 195 may have a shroud 196 that houses an illumination component 197 and a sensing component 198. A cable 194 can connect to the 3D scanner to the processor 190. Connected to the shroud 196 of the 3D scanner is the scanner element 105, or probe, which includes lenses 106 to focus light. The illumination component 197 produces light that excites the fluorescent material in the inflatable membrane, as well as light that may allow for general viewing of the cavity being scanned and the area around the cavity, such as when locating an area of interest. The light generated by the illumination component 197 for general viewing may be white light generated by one or more light source, such as one or more light emitting diodes. The light generated by the illumination components 197 for excitation of the fluorescent material in the inflatable membrane may be blue light generated by one or more light source, such as one or more light emitting diodes. The sensing component 198 may include one or more of a mirror, a beam-splitter, a filter, and multiple detectors. Each detector sends data to the processor 190 through the cable 194. The data from the one or more sensors may be combined, multiplexed, or otherwise processed before it is sent through the cable 194. The processor 190 may send commands, such as illumination, scanning, or focusing instructions, to the front-end of the 3D scanner through the cable 194. The configuration the components of the front-end of the 3D scanner shown in FIG. 1F is a representative configuration. The 3D scanner may have an illumination component 197, sensing component 198, probe 105, and processor 190 in other configurations suitable for scanning a cavity, such as an anatomical cavity.

Referring again to FIG. 1D, to determine distance from the scanner element 105 and a corresponding surface of the interior of membrane 110, the ratio of the intensity of two or more wavelengths or ranges of wavelengths may be used. Specifically, the intensity of the light emitted by the fluorescent material may be measured and recorded for at least two wavelengths, $\lambda_1$, $\lambda_2$, or ranges of wavelengths, one of which is the wavelength or wavelength range that is preferentially absorbed by the absorbing medium. The ratio of the intensity of two or more wavelengths or ranges of wavelengths, at least one of which is preferentially absorbed by the absorbing medium, allows the 3D scanner 195 and/or processor 190 to calculate the distance between the fluorescent material of the inflatable membrane 110 and the distal tip of the scanner element 105 that receives the light 125, 130 from the fluorescent material. The light 115 from the scanner element 105 may scan the inner surface of the membrane 110 by illuminating points or areas on the inflatable membrane 110 in a sequential manner, so that an array of ratios of intensities of the wavelengths, and thus distances, corresponding to points on the inflatable membrane 110 can be created. As noted above, the scanner element 105 may move within the membrane 110 to allow illuminating portions along some, if not all, of the entire inner surface of the membrane 110.

The 3D scanner 195 may include a spectrometer to measure intensities for the two or more wavelengths or ranges of wavelengths of light from the fluorescent material. The wavelengths of light that can be compared include red light (such as light with wavelength ranging from about 620 to about 750 nanometers (nm)) and green light (such as light with wavelength ranging from about 495 to about 570 nm). Additionally, or alternatively, the intensity of other wavelengths of light can be measured and compared, such as any combination of violet light (approximately 380 to 450 nm), blue light (approximately 450 to 495 nm), green light (approximately 495 to 570 nm), yellow light (approximately 570 to 590 nm), orange light (approximately 590 to 620 nm), and red light (620-750 nm). The spectrometer can include one or more detectors, such as CCD (charge coupled device) or CMOS (complementary metal-oxide semiconductor) detectors, to measure the intensity of light, as well as implements to select the wavelengths to be measured, such as one or more grating, beam splitter, or filter.

The 3D scanner 195 may also measure the intensity of one or more wavelengths or ranges of wavelengths of light from fluorescent material embedded in, or on, the inflatable membrane as a function of the degree of inflation of the membrane. That is to say, the inflatable membrane can be inflated to multiple levels of inflation while inside of an anatomical cavity, and measurements of the intensity of one or more wavelengths or ranges of wavelengths of light emitted from fluorescent material embedded in or on the inflatable membrane can be recorded and used to determine at least a 3D image or a surface topography of the anatomical cavity corresponding to this one or more levels of inflation. In the case of the human ear, particularly the aural canal, the size of the canal and compliance of the tissue in the canal can be determined, and the location of anatomical features, such as the bone-cartilage junction, can be found. Knowledge of the shape, compliance, and location of anatomical features can be used to create a device that provides better sound transmission, more comfort to a device user, or for the development of device materials. In some example implementations, the membrane 110 may be dynamically inflated to different pressures to enable the 3D scanner 195 to better scan certain anatomical features, such as the bone-cartilage junction and the like. This may be aided by asking the patient to move her anatomical features, for example by chewing, during the scan, and by observing changes in measurements as a function of this anatomical feature displacement.

The 3D scanner 195 may, as noted above, excite points or portions of the inflatable membrane in a sequential manner to obtain data that allows for the determination of the shape and mechanical properties, such as compliance, of the anatomical cavity surrounding the inflatable membrane. The scan method and path, or sequence of points selected by the user or the system, can be chosen to improve accuracy, speed, or repeatability of the measurements made by the system. For example, 3D scanner 195 including the scanning elements 105 may be configured to allow scanning in a variety of methods and patterns to obtain as accurate a rendering of the anatomical cavity as possible. Such methods and scan patterns may include a hub-and-spoke pattern, a spiral pattern, and/or any other method or pattern.

In order to stitch two or more images (for example, scanner data collected by scanner element 105 at two portions of the cavity) into a 3D image or surface, fiducial markers may be placed on the interior surface of membrane 110, so that these fiducial markers can be located during processing of the scan data (for example, scanned images of portions of the ear cavity 182). These fiducial markers may serve as so-called landmarks in the scan images, so that a processor can combine the data/images based on the fiducial marks. The scanned images may represent an image, data, and/or any information representative of the surface of the interior membrane (and thus the cavity being scanned).

In the case of scanner element 105, fluorescent imaging through medium 120 may, as noted, selectively absorb one wavelength or range of wavelengths of light over another, and this selective absorption may be used to determine depth from scanner element 105 to the fluorescent membrane 110. This depth measurement may, as noted, be based on a ratio of the absorbed-to-transmitted wavelengths or ranges of wavelengths of light. Moreover, a processor may correlate the depth measurement to the corresponding scan data/images. For example, a portion of the 2D scanner image of the fluorescent membrane 110 may be correlated to a depth measurement determined from the ratio of the absorbed-to-transmitted wavelengths of light. In this way, the 2D scanner data/image is processed into a 3D image or surface. Because the fiducial markers represent a known pattern on the surface of the membrane 110, the fiducial markers may be used to register and thus determine the location of each of the scanned image frames on membrane 110.

In some example embodiments, there may be provided processes for providing fiducial marks on the interior surface of membrane 110.

Figure 2A:
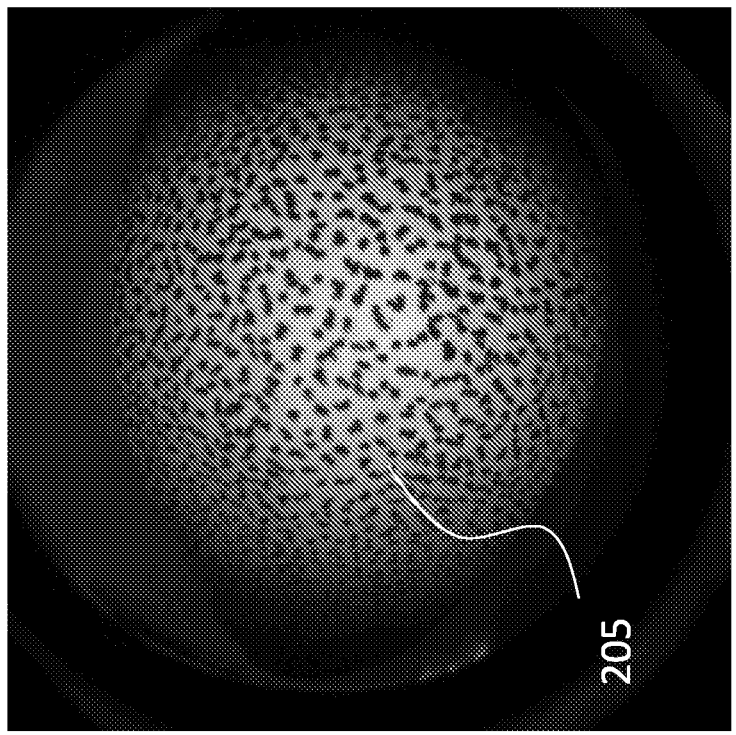
FIGS. 2A-2B depict examples of pad-printed fiducial markers.

In some example embodiments, fiducial marks may be provided on membrane 110 using a pad-printing process. FIG. 2A depicts an example of a fiducial pattern 205 on the interior surface of membrane 110, in accordance with some example embodiments. The pattern may be a known pattern that can be decoded by processor 190 to determine location on the interior surface of membrane 110. This location information may allow processor 190 to combine different (including overlapping) images of the interior surface of membrane 110.

In some example embodiments, a dark silicone dye may be pad-printed onto membrane 110 (which may have previously been embedded with at least a fluorescent dye) to produce fiducial markers 205. The printed fiducial pattern may be configured to be sparse enough so that the fiducial markers do not substantially interfere with the fluorescent properties of the underlying fluorescent membrane. The printed fiducial pattern may, however, be configured to be dense enough to provide sufficient feature richness and detection in the scanner data/images collected by the scanner element 105. Moreover, the fiducial pattern may be pad-printed with various marker sizes, pattern geometry, and the like to satisfy dense ad sparse constraints. Another way of varying the density is to modify the silicone dye's surface tension. This approach may alter adhesion and the size of the pad-printed object on the membrane.

Moreover, the curing schedules of the pad-printed fiducial markers may also be varied to satisfy dense and/or sparse constraints (as well as to ensure that the fiducial markers remains adhered to the membrane during inflation and exposure to solvents and expected environmental conditions for the desired shelf life of the device).

Figure 2B:
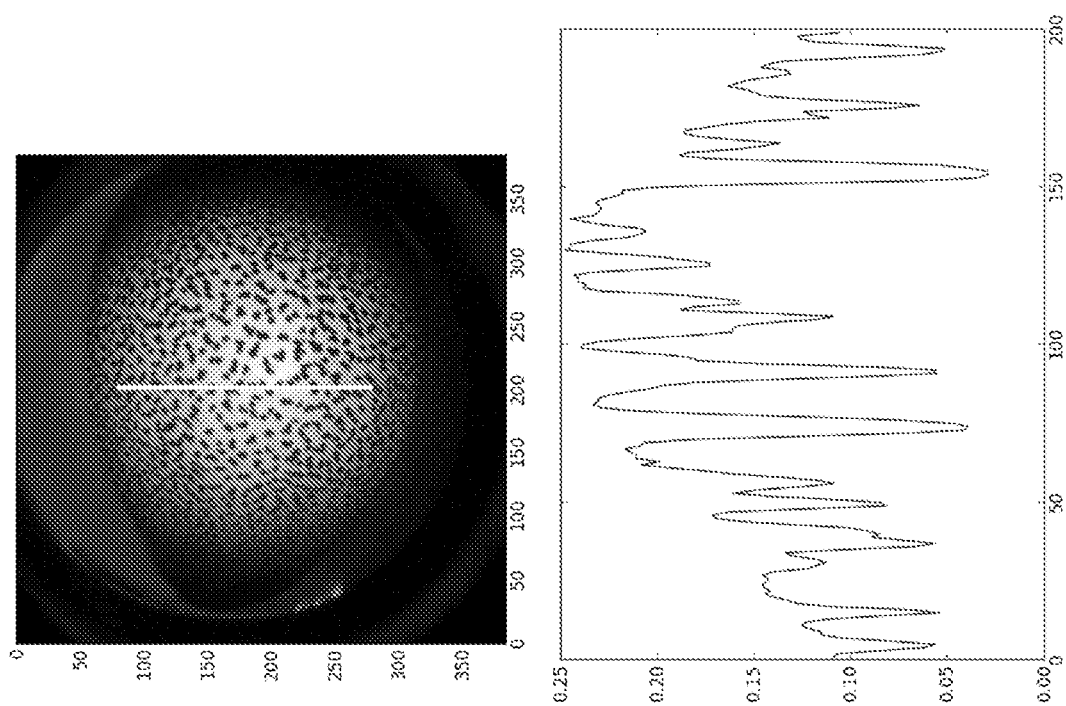

FIG. 2B depicts pad-printed fiducial markers of FIG. 2A with a corresponding plot showing the variation in green light intensity units. This variation in intensity shows the ability of the system to distinguish fiducial marks from regions of the membrane that are not fiducial marks.

Figure 3A:
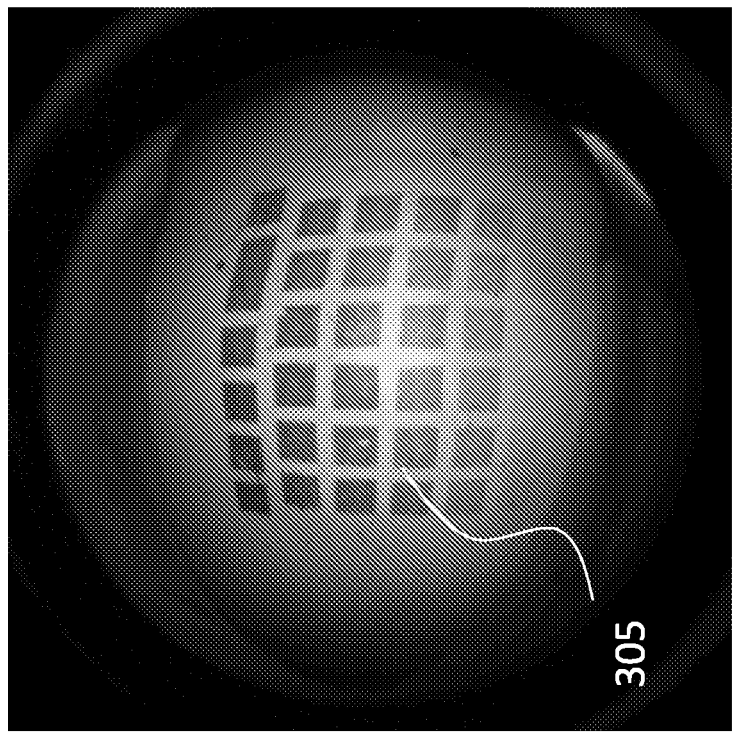
FIG. 3A-3B depict examples of photo-bleached fiducial markers.

In some example embodiments, fiducial marks may be provided on membrane 110 using a photo-bleaching process. FIG. 3A depicts an example of a fiducial marker pattern 305 that has been photo-bleached on the interior surface of membrane 110, in accordance with some example embodiments.

For example, membrane 110 may be photo-bleached to generate fiducial markers 305 to appear on membrane 110. To illustrate, a laser, such as an ultraviolet laser, may be used to mark a specific surface pattern 305 onto membrane 110. The laser may thus photobleach a known pattern into the membrane 110 to photo-bleach the membrane 110 embedded with fluorescent dye. Membrane 110 may be implemented as for example a silicon-based balloon, in which case the balloon may be placed flat (or placed on a mandrel), so that a high-energy ultraviolet light can cause the fluorophore in the membrane 110 to exhaust its fluorescent lifetime—thereby preventing membrane 110 from emitting its typical emission wavelength of light when it is subsequently excited.

The photo-bleaching process may prevent the fiducial marker pattern from peeling off the membrane 110, and may prevent loss/removal of the pattern due to applied solvents, such as alcohol. Because the photo-bleaching process may affect primarily the surface of membrane 110, photo-bleaching may not affect the mechanical properties of the membrane 110.

Figure 3B:
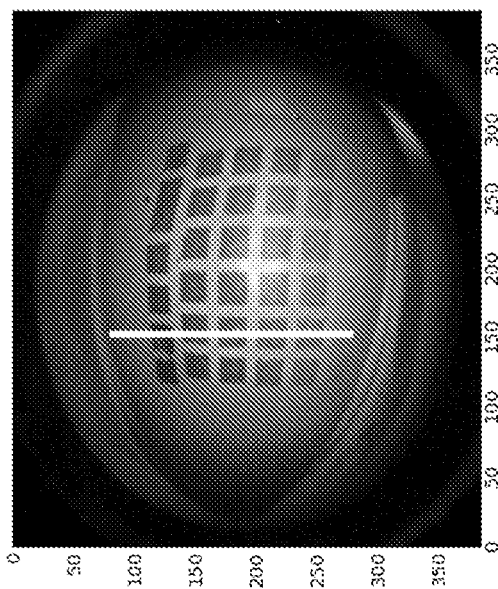
Figure 3B:
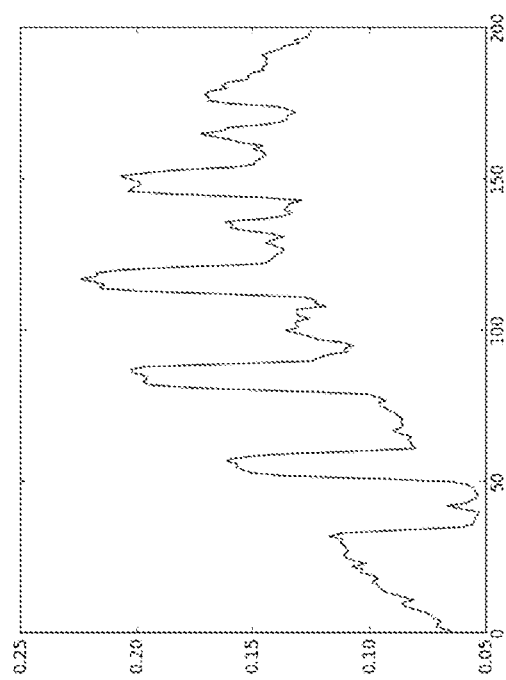

FIG. 3B depicts the pad-printed fiducial markers 305 of FIG. 3A with a corresponding plot of the showing the variation in green light intensity units. This variation in intensity may show the ability of the 3D scanner system to distinguish fiducial marks from regions of the membrane that are not fiducial marks.

In some example embodiments, fiducial marks may be provided on the membrane 110 by mixing large fluorescent dye particle into the material composition of membrane 110, in which case the pattern formed by the fiducial marks may be a predetermined pattern, such as a random pattern or semi-random pattern, that can be detected by the processor.

Figure 4:
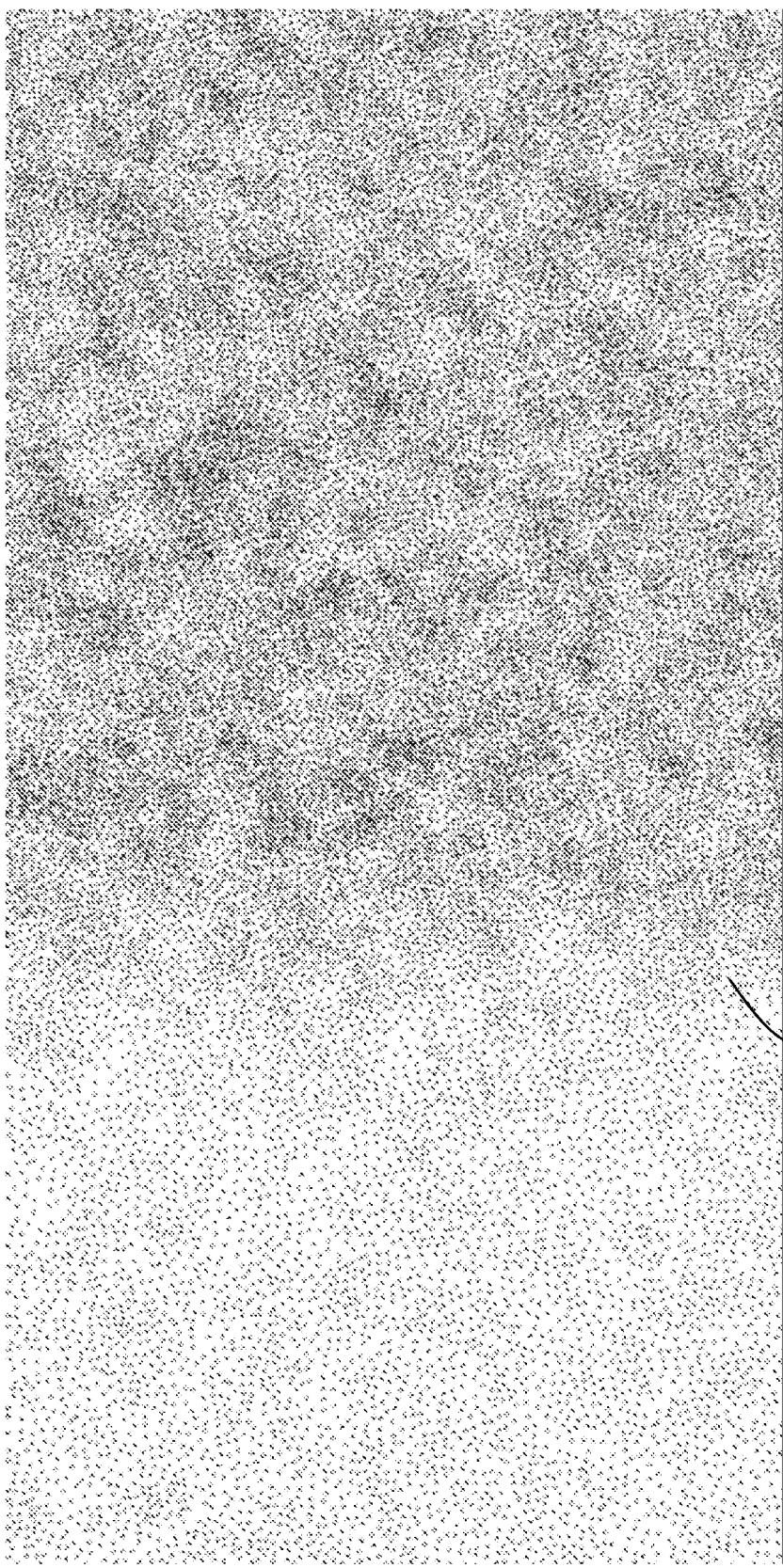
FIG. 4 depicts an example of a random fiducial marker pattern.

FIG. 4 depicts an example of a random fiducial marker 405 pattern on the interior surface of membrane 110, in accordance with some example embodiments. The scanner may stitch adjacent images together with or without a priori knowledge of the fiducial marks. When this is the case, if a scanner images two 2D images and detects an area of overlap including an area of the same fiducial marks between the two images, the scanner may be able to align the corresponding matching fiducial marks and stitch the two images together.

Figure 5A:
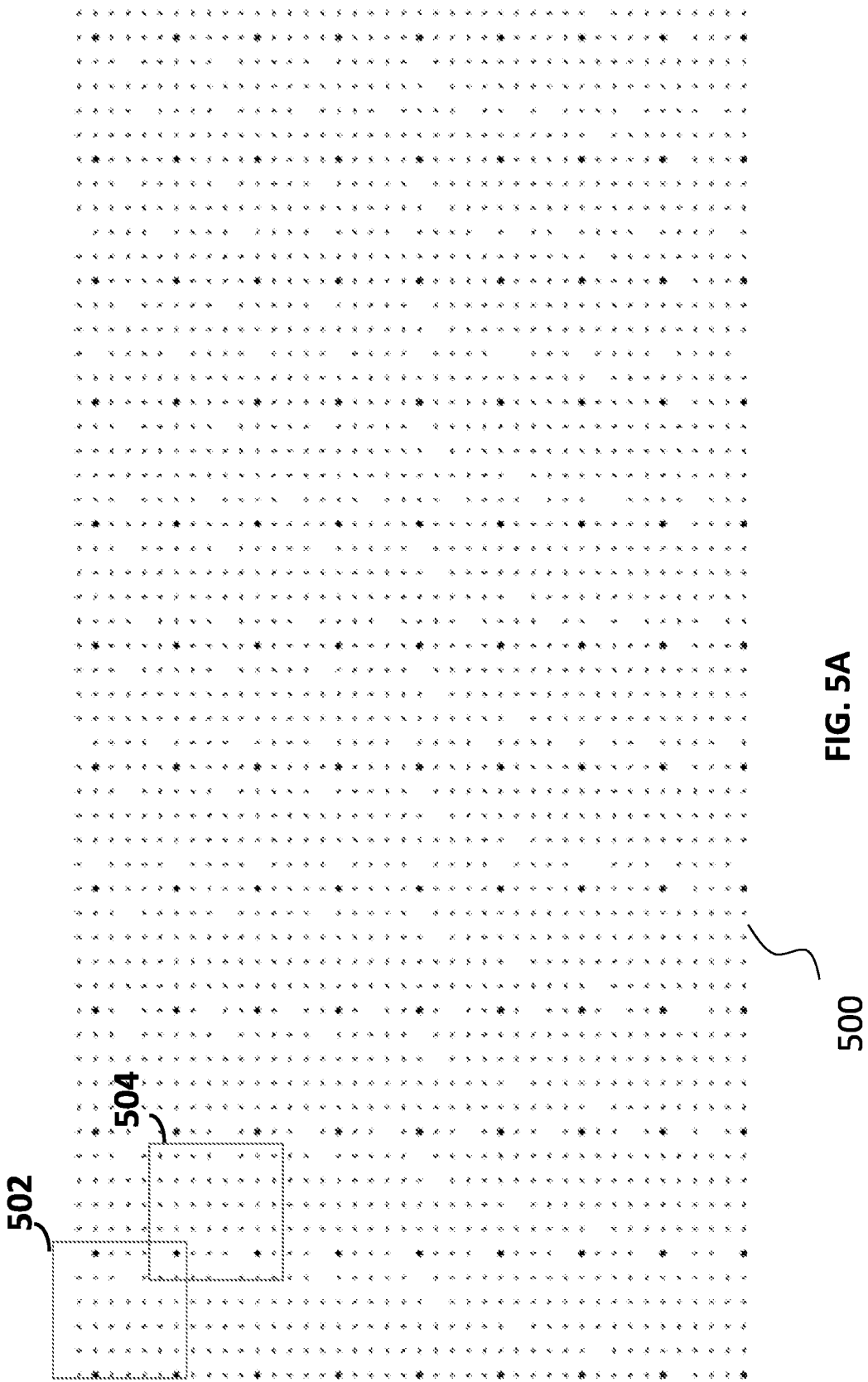
FIGS. 5A-5E depict examples of fiducial marker patterns that encode location information.

FIG. 5A depicts an example of fiducial markers forming a known pattern 500, in accordance with some example embodiments. The pattern 500 may be placed on the interior of the membrane 110 using for example pad-printing, photobleaching, and/or any other application method. The interior refers to the interior surface of membrane 110, which is being scanned by scanner element 105.

The pattern 500 may include a known and/or predetermined pattern having location information encoded in the pattern 500 itself. Specifically, each portion of the pattern 505 may include location information. This location information may enable a processor to determine where the portion is located in the pattern and thus the interior membrane 110. A processor may then use the location information to combine the portion with other portions.

For example, when scanner element 105 scans a frame 502 of the interior of the membrane, a processor may detect from the scan data/image the presence of the fiducial marker pattern (which includes first location information identifying a relative location within pattern 500 and thus on the membrane 110). Likewise, when scanner element 105 scans a frame 504, the processor may detect from the scan data/image the presence of the fiducial marker pattern therein (which includes second location information identifying a relative location within pattern 500 and thus on the membrane 110). The processor may, based on the location information, place each scanned frame in its proper position relative to other frames in order to combine or stitch together the frames to form a 2D or 3D image (or surface).

Figure 5B:
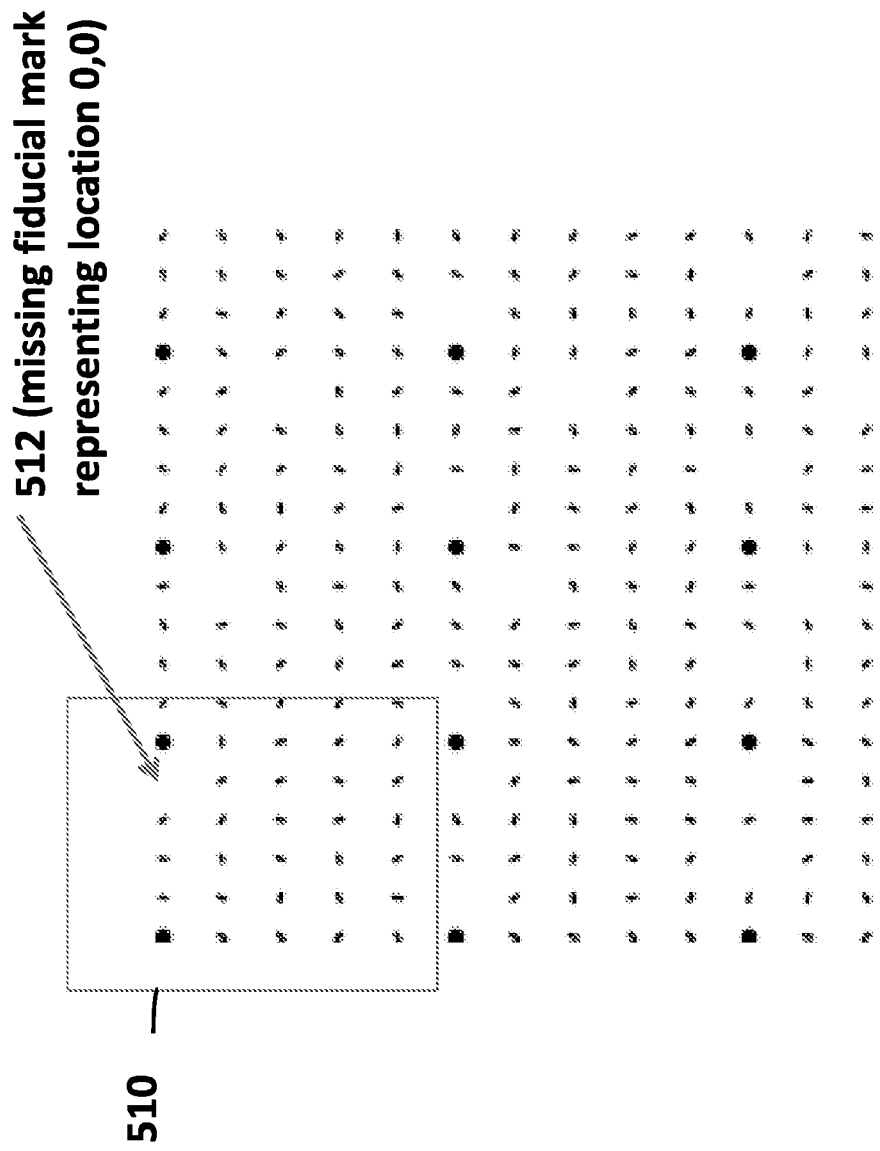
Figure 5C:
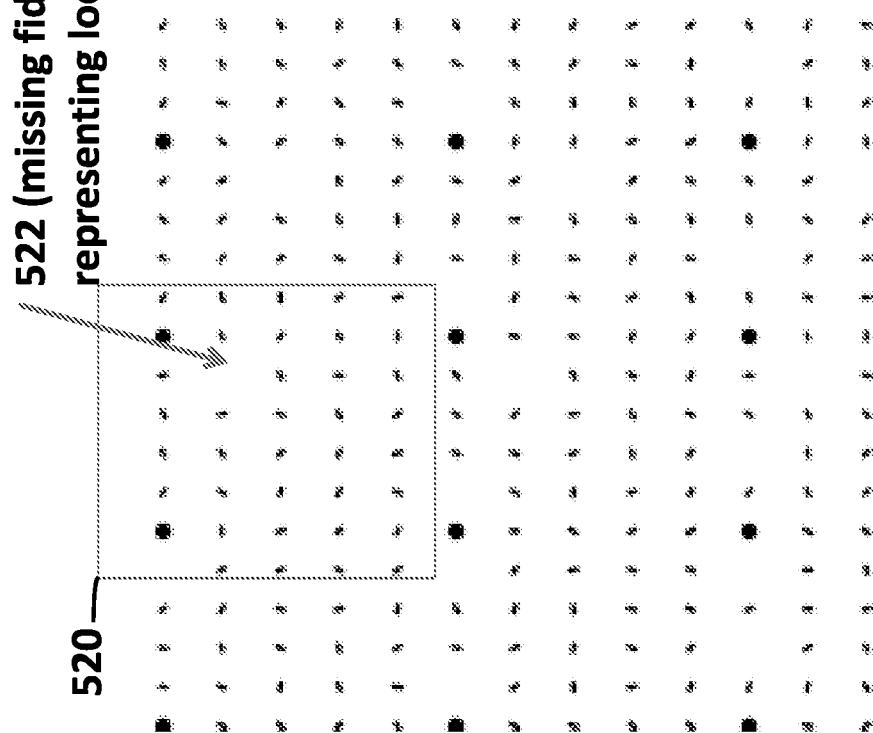
Figure 5D:
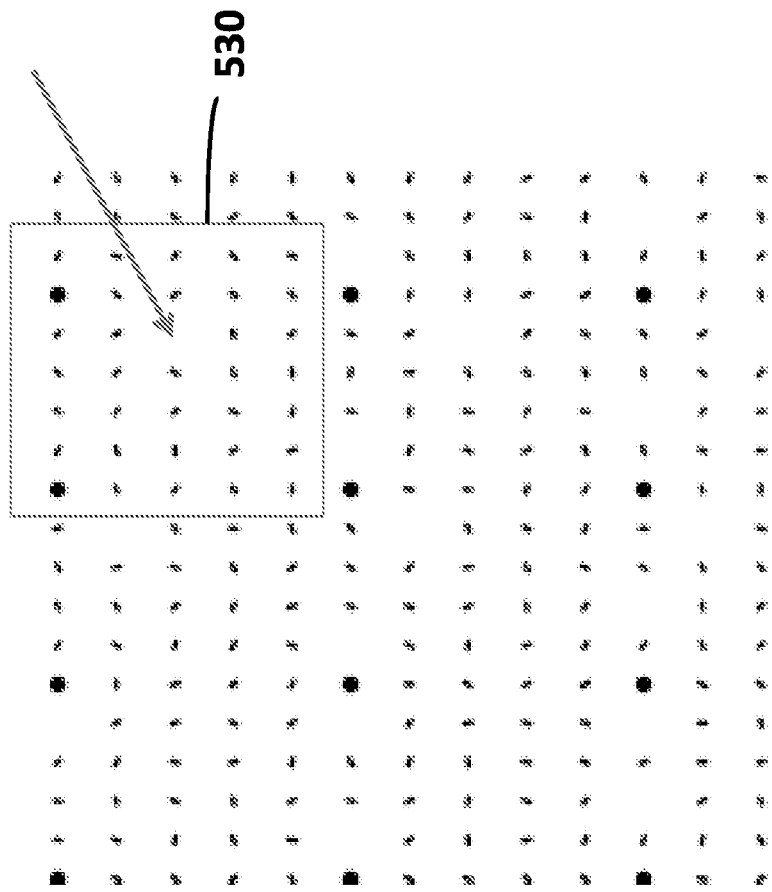
Figure 5E:
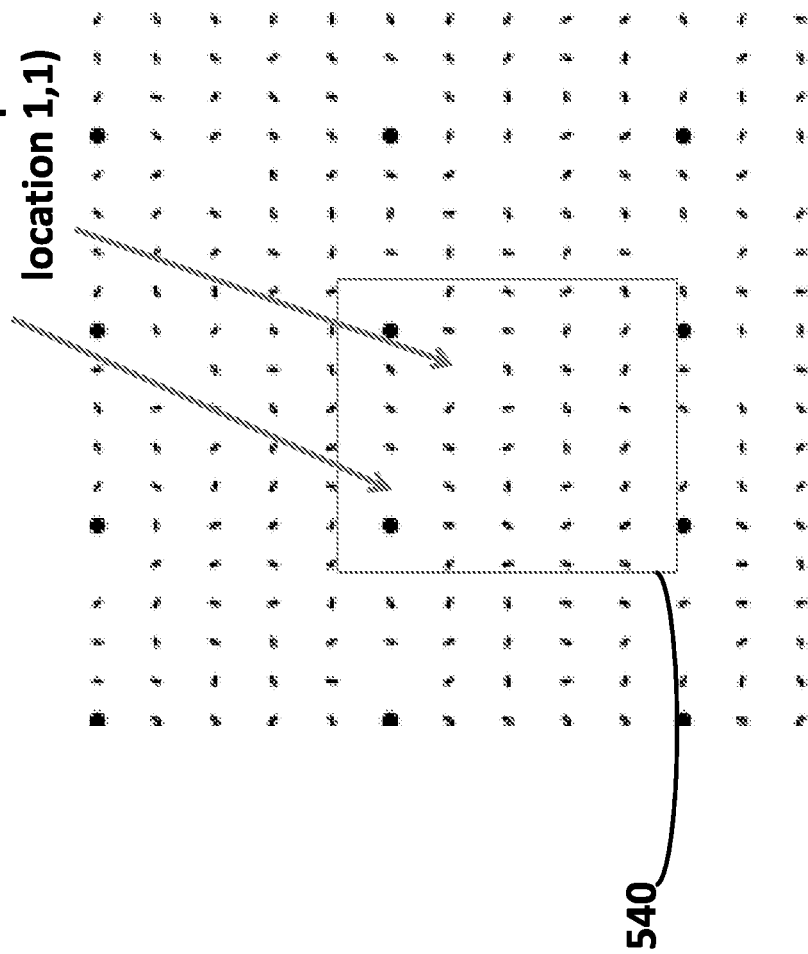

FIG. 5B depicts a subset of the pattern 500 corresponding generally to the top left-hand portion of pattern 500 of FIG. 5A. In the example of FIG. 5B, if a frame of scan data includes frame 510, a processor may detect the fiducial markers in the scan/image data and then decode the fiducial markers to determine the location of that frame based on location information coded (or embedded) in the fiducial pattern itself. For example, the location of the missing fiducial mark may correspond to location 0, 0 (which represents relative location information on the fiducial pattern and thus on the membrane 110). FIG. 5C depicts frame 520. In 520, the missing fiducial mark may correspond to location 0, 1 (which also represents a relative location information on the fiducial pattern and thus on the membrane 110). FIG. 5D depicts another frame 530, which may correspond to 0, 2; FIG. 5E depicts frame 540, which may correspond to location 1, 1; and so forth. In this way, different frames comprising different (including overlapping) scan data/images may be combined given the location information contained in the fiducial marks. A processor may thus be able to stitch (or combine) the frames 510-540 as well as other frames from different portions of the scanned cavity to form a larger 2D or 3D image/surface representation of the cavity. FIG. 5F depicts an example of frames 510-540 stitched (or combined) based on the location information contained in the fiducial marker pattern.

Although the fiducial markers depicted in FIGS. 5A-5E use the location of missing markers to encode location, the location may be encoded in other ways as well. For example, shape and orientation of fiducials, preprogrammed knowledge of the location of the fiducials, color of the fiducials, density and sparseness of the fiducials and/or the like.

In some example embodiments, fiducial markers may be configured using a plurality of small geometric features, such as circles, crosses, squares, triangles, and the like that overlap with one another in a random orientation, as depicted at FIG. 4, in order to make a unique marker for image recognition.

The pattern at FIG. 4 may include sufficient surface area to allow for pad-printing ink to overcome surface tension and adhere to the membrane. If features are too small (for example, less than about 0.003" in diameter), the pad-printed fiducial marker may not adhere to the membrane material in some implementations. The pattern at FIG. 4 may show the density and sparseness variations along the length of the membrane that provide enough density for fiducials to be present, as well as enough sparseness for the underlying fluorescent membrane to be present. It may show the variation of this sparseness and density that changes over the length of the membrane to compensate for the expected amount of inflation of the membrane as well as the angle of view of various portions of the membrane during a normal scan.

In some example embodiments, the actual individual fiducial markers may have an aspect ratio of greater than 1 and a specific orientation that differs from that of neighboring markers. This may be used in conjunction with an overlaid grid of larger markers. Relatively large markers may be more easily detected and reduce computation time during image processing, while the smaller markers with the large aspect ratio and fixed orientation may allow for the fine-tuning of the matching of fiducial markers for image stitching. An example of such a pattern is shown in FIG. 5B where the oval shaped features have an aspect ratio that is not 1 and differing orientations.

In some example embodiments, the ratio of absorbed-to-transmitted wavelengths of light may be configured using the pad printing and/or photo-bleaching processes described above with respect to FIGS. 2B and 3B. With these altered ratios, it may be possible to gain more accurate depth information during imaging by using this additional information. That is, a second distance versus red/green (or other pair of colors or color ranges) light ratio may be generated for the photo-bleached or pad-printed regions. The image intensity may then be utilized wherever fiducial markers are located on the membrane. This additional depth data may provide higher accuracy for the 3D imaging. A fractal pattern of dark and light regions may also be used in the fiducial markers to provide a signal but still provide image features. That is, instead of pad printing dots, a fractal pattern may be pad printed, and this pattern may include features at a large scale and/or a small scale. This may, in some implementations, provide density and sparseness as previously described In some implementations, the medium 120 may be configured and/or optimized based on depth measurements of marked and unmarked regions of the membrane 110. That is, the relationship between depth and ratio of wavelengths or ranges of wavelengths may be known for the bare fluorescent membrane as well as for the membrane with the fiducial markers in place. By knowing this information, depth information may be obtained from the membrane even in the location that there are fiducial markers.

In some example embodiments, one or more processors, such as processor 190 may include program code to cause receiving a first data representative of a first scanned portion of an interior surface of a balloon membrane and a second data representative of a second scanned portion of the interior surface of the balloon membrane, the interior surface including a pattern comprising one or more fiducial markers. The processor 190 configured with code may also detect from the first data a first portion of the pattern, the first portion indicating a location of the first portion within the pattern and the interior surface of the balloon membrane. For example, the data sets may be processed to detect the patterns from the data set. The processor 190 configured with code may also detect from the second data a second portion of the pattern, the second portion indicating another location of the second portion within the pattern and the interior surface of the balloon membrane. The processor 190 configured with code may also combine, based on the first portion of the pattern and the second portion of the pattern, the first data and the second data to form a three dimensional representation of the interior surface.

The subject matter described herein may be embodied in systems, apparatus, methods, and/or articles depending on the desired configuration. For example, the scanning system (or one or more components therein) and/or the processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the phrase "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. In various example implementations, the methods (or processes) can be accomplished on mobile station/mobile device side or on the server side or in any shared way between server and user equipment/mobile device with actions being performed on both sides. The phrases "based on" and "based on at least" are used interchangeably herein. Other implementations may be within the scope of the following claims.

What is claimed:
1. An apparatus comprising:
a balloon membrane comprising an opening, an exterior surface, and an interior surface,
    wherein the interior surface of the balloon membrane comprises one or more fiducial markers forming a predetermined pattern,
    wherein portions of the predetermined pattern comprise encoded information of an absolute location on the interior surface of the balloon membrane and wherein the encoded information is electronically readable,
    wherein a first portion of the predetermined pattern comprises encoded information of a first location on the interior surface of the balloon membrane and a second portion of the predetermined pattern comprises encoded information of a second location on the interior surface of the balloon membrane; and
    wherein portions of the balloon membrane having the one or more fiducial markers and portions of the balloon membrane without the one or more fiducial markers are configured for different ratios of absorption of two different wavelengths of light;
a scanner coupled to the opening of the balloon membrane, wherein the scanner images a plurality of portions of the interior surface of the balloon membrane, including the one or more fiducial markers forming the predetermined pattern when the balloon membrane is inflated with a wavelength-selective medium;

wherein the first portion of the predetermined pattern is included in a first imaged frame of the interior surface of the balloon membrane and the second portion of the predetermined pattern is included in a second imaged frame of the interior surface of the balloon membrane, wherein the scanner calculates a distance through the wavelength-selective medium to a point on the interior surface of the balloon membrane based on a ratio of absorption of two different wavelengths of light, and wherein the scanner determines depth information using a first ratio of absorption for the portions of the balloon membrane with the one or more fiducial markers and a second ratio of absorption for the portions of the balloon membrane without the one or more fiducial markers, and wherein a three-dimensional representation of the interior surface of the balloon membrane is formed by the depth information and electronically reading and decoding the encoded information included in the first imaged frame and the second imaged frame by a processor.

2. The apparatus of claim 1, wherein the one or more fiducial markers forming the predetermined pattern encode location information indicating relative locations within the predetermined pattern.

3. The apparatus of claim 2, wherein the location information is encoded based on at least one missing fiducial marker.

4. The apparatus of claim 3, wherein the at least one missing fiducial marker indicates a relative location on the predetermined pattern and on the interior surface of the balloon membrane.

5. The apparatus of claim 1, wherein the one or more fiducial markers are applied to the interior surface of the balloon membrane by at least one of pad-printing or photo-bleaching.

6. The apparatus of claim 1, wherein the predetermined pattern comprises fiducial markers of different sizes and wherein the predetermined pattern includes smaller fiducial markers with an overlaid grid of larger fiducial markers.

7. A method comprising:
  encoding, within a pattern of fiducials, information of an absolute location on an interior surface of a membrane to form an encoded pattern, wherein a first portion of the encoded pattern comprises encoded information of a first location on the interior surface of the membrane and wherein a second portion of the encoded pattern comprises encoded information of a second location on the interior surface of the membrane wherein the encoded information of the first location and the encoded information of the second location is electronically readable, and
  wherein portions of the membrane having the pattern of fiducials and portions of the membrane without the pattern of fiducials are configured for different ratios of absorption of two different wavelengths of light;
  generating, by a scanner coupled to an opening of the membrane, a first imaged frame of the interior surface of the membrane and a second imaged frame of the interior surface of the membrane, wherein the scanner images a plurality of portions of the interior surface of the membrane including the first imaged frame and the second imaged frame, when the membrane is inflated with a wavelength-selective medium,
    wherein the scanner calculates a distance through the wavelength-selective medium to a point on the interior surface of the membrane based on a ratio of absorption of two different wavelengths of light, and
    wherein the scanner determines depth information using a first ratio of absorption for the portions of the membrane with the pattern of fiducials and a second ratio of absorption for the portions of the membrane without the pattern of fiducials;
  receiving a first data representative of the first imaged frame of the interior surface of the membrane and a second data representative of the second imaged frame of the interior surface of the membrane;
  electronically reading and decoding the first portion of the encoded pattern included in the first imaged frame to reveal that the first imaged frame corresponds to the first location on the interior surface of the membrane;
  electronically reading and decoding the second portion of the encoded pattern included in the second imaged frame to reveal that the second imaged frame corresponds to the second location on the interior surface of the membrane; and
  forming a three-dimensional representation of the interior surface of the membrane by at least combining, based at least on respective decoded locations of the first imaged frame and the second imaged frame, the depth information, the first data and the second data.

8. The method of claim 7, wherein the fiducials forming the encoded pattern encode location information indicating relative locations within the pattern.

9. The method of claim 8, wherein the location information is encoded based on at least one missing fiducial marker.

10. The method of claim 9, wherein the at least one missing fiducial marker indicates a relative location on the encoded pattern and on the interior surface of the membrane.

11. The method of claim 7, wherein the fiducials are applied to the interior surface of the membrane by at least one of pad-printing or photo-bleaching.

12. A non-transitory computer-readable storage medium including code, which when executed by at least one processor circuitry provided operations comprising:
  receiving a first data representative of a first imaged frame of an interior surface of a membrane inflated with a wavelength-selective medium and a second data representative of a second imaged frame of the interior surface of the membrane inflated with a wavelength-selective medium, wherein the interior surface includes one or more fiducial markers forming an electronically readable encoded pattern, wherein a first portion of the encoded pattern comprises encoded information of a first absolute location on the interior surface of the membrane, wherein a second portion of the encoded pattern comprises a second absolute location on the interior surface of the membrane, and wherein the first imaged frame includes the first portion of the encoded pattern and the second imaged frame includes the second portion of the encoded pattern, wherein portions of the membrane having the one or more fiducial markers and portions of the membrane without the one or more fiducial markers are configured for different ratios of absorption of two different wavelengths of light;
  calculating a distance through the wavelength-selective medium to a point on the interior surface of the membrane based on a ratio of absorption of two different wavelengths of light, and determining depth information using a first ratio of absorption for the portions of the membrane with the one or more fiducial markers and a second ratio of absorption for the portions of the membrane without the one or more fiducial markers;

electronically reading and decoding the first portion of the encoded pattern included in the first imaged frame to reveal that the first imaged frame corresponds to the first absolute location on the interior surface of the membrane;

electronically reading and decoding the second portion of the encoded pattern included in the second imaged frame to reveal that the second imaged frame corresponds to the second absolute location on the interior surface of the membrane; and forming a three-dimensional representation of the interior surface of the membrane by at least combining, based at least on respective decoded locations of the first imaged frame and the second imaged frame, the depth information, the first data and the second data.

13. The apparatus of claim 1, wherein the predetermined pattern includes a first fiducial marker that is smaller relative to a second fiducial marker, wherein the second fiducial marker is adapted to facilitate an initial determination of respective decoded locations of the first imaged frame and the second imaged frame, and wherein the first fiducial marker is adapted to enable a fine-tuning of the initial determination of the respective decoded locations of the first imaged frame and the second imaged frame.

14. The method of claim 7, wherein the encoded pattern comprises at least one of a shape, a size, an orientation, a density, or a color of the fiducials.

* * * * *